(12) United States Patent
Wang

(10) Patent No.: US 11,207,204 B2
(45) Date of Patent: Dec. 28, 2021

(54) NECK COLLAR

(71) Applicant: Yu-Chien Wang, Taichung (TW)

(72) Inventor: Yu-Chien Wang, Taichung (TW)

(*) Notice: Subject to any disclaimer, the term of this patent is extended or adjusted under 35 U.S.C. 154(b) by 321 days.

(21) Appl. No.: 16/566,404

(22) Filed: Sep. 10, 2019

(65) Prior Publication Data
US 2021/0069002 A1 Mar. 11, 2021

(51) Int. Cl.
A61F 5/055 (2006.01)
A61F 5/01 (2006.01)

(52) U.S. Cl.
CPC ...... A61F 5/055 (2013.01); A61F 2005/0197 (2013.01)

(58) Field of Classification Search
CPC .. A61F 5/055; A61F 5/04; A61F 5/042; A61F 5/048; A61F 5/05; A61F 5/05883; A61F 5/05816; A61F 5/05833
USPC .......................................................... 602/18
See application file for complete search history.

(56) References Cited

U.S. PATENT DOCUMENTS

| | | | | |
|---|---|---|---|---|
| 2012/0130295 A1* | 5/2012 | Haider | ............... | A61F 5/055 602/18 |
| 2012/0165712 A1* | 6/2012 | Calabrese | ............... | A61F 5/055 602/18 |
| 2013/0261519 A1* | 10/2013 | Garth | ............... | A61F 5/055 602/18 |
| 2013/0281900 A1* | 10/2013 | Suarez | ............... | A61F 5/055 602/18 |
| 2013/0310722 A1* | 11/2013 | Thorsteinsdottir | ............... | A61F 5/05883 602/18 |
| 2015/0190266 A1* | 7/2015 | Hollern | ............... | A61F 5/055 602/18 |
| 2016/0008158 A1* | 1/2016 | Martin | ............... | A61F 5/055 602/18 |
| 2016/0058601 A1* | 3/2016 | Garth | ............... | A61F 5/055 602/18 |

* cited by examiner

Primary Examiner — Tarla R Patel
(74) Attorney, Agent, or Firm — Muncy, Geissler, Olds & Lowe, P.C.

(57) ABSTRACT

A neck collar is provided, including: a neck sleeve, a chin support and an adjustment mechanism. The chin support is swingably connected to the neck sleeve. The adjustment mechanism includes at least one linking member and at least one driving member with which the linking member is co-movably connected. Each of the at least one linking member is movably connected to the neck sleeve and movably abutted against the chin support. The at least one driving member is externally operable and adjustable to drive the at least one linking member to move relative to the neck sleeve and to move relative to the chin support, simultaneously, between a first position and a second position. When the at least one linking member is moved toward the second position, the at least one linking member drives the chin support to swing upwardly relative to the neck sleeve.

6 Claims, 7 Drawing Sheets ic strength around the at least one guiding groove 11.

NECK COLLAR

BACKGROUND OF THE INVENTION

Field of the Invention

The present invention relates to a neck collar.

Description of the Prior Art

A neck collar is used to support an injured neck of a patient so as to reduce burden on the neck and avoid getting injured again due to unexpected movement of head and neck. Generally, a chin support of the neck collar is swingable relative to the neck sleeve so as to meet various using requirements.

The chin support of a conventional neck collar is usually adjustable by strips, cables or the like. For easy operation, each of the strips is wound around a pivot and connected to the chin support so that the strips drive the chin support to swing upwardly when the strips are pulled down. However, a structure of the conventional neck collar as described above is complicated and inconvenient to assemble, and the conventional neck collar is inconvenient to be repaired or maintained when its components are damaged. In addition, each of the strips is directly connected to the chin support in a manner of single-point connection, which results in unsmooth movement due to small forced area.

The present invention is, therefore, arisen to obviate or at least mitigate the above-mentioned disadvantages.

SUMMARY OF THE INVENTION

The main object of the present invention is to provide a neck collar which has a simple structure and is smoothly adjustable.

To achieve the above and other objects, the present invention provides a neck collar, including: a neck sleeve, a chin support and an adjustment mechanism. The chin support is swingably connected to the neck sleeve. The adjustment mechanism includes at least one linking member and at least one driving member with which the at least one linking member is co-movably connected. Each of the at least one linking member is movably connected to the neck sleeve and movably abutted against the chin support. The at least one driving member is externally operable and adjustable to drive the at least one linking member to move relative to the neck sleeve and to move relative to the chin support, simultaneously, between a first position and a second position. When the at least one linking member is moved from the first position toward the second position, the at least one linking member drives the chin support to swing upwardly relative to the neck sleeve.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
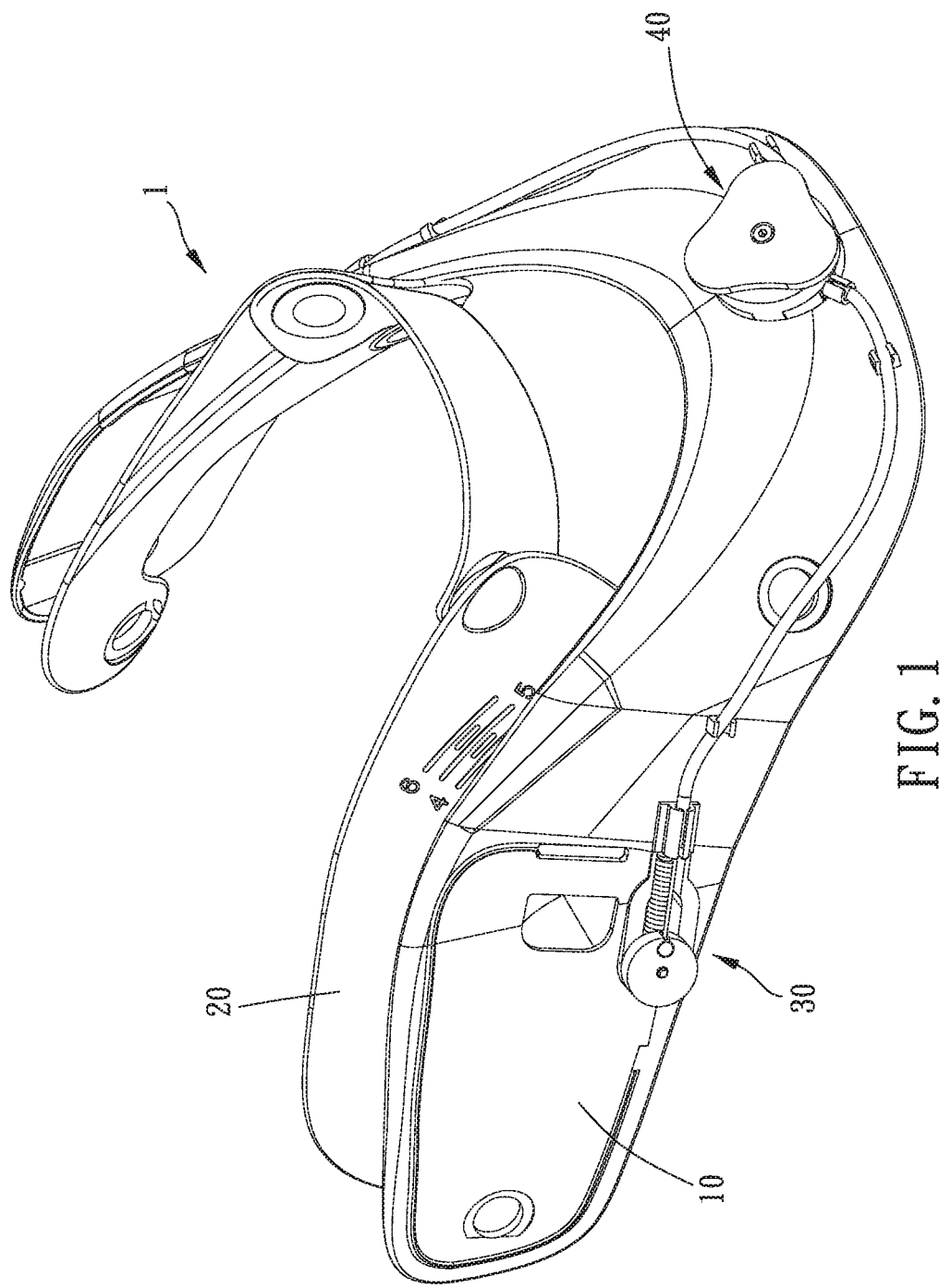
FIG. 1 is a stereogram of a preferable embodiment of the present invention.
Figure 2:
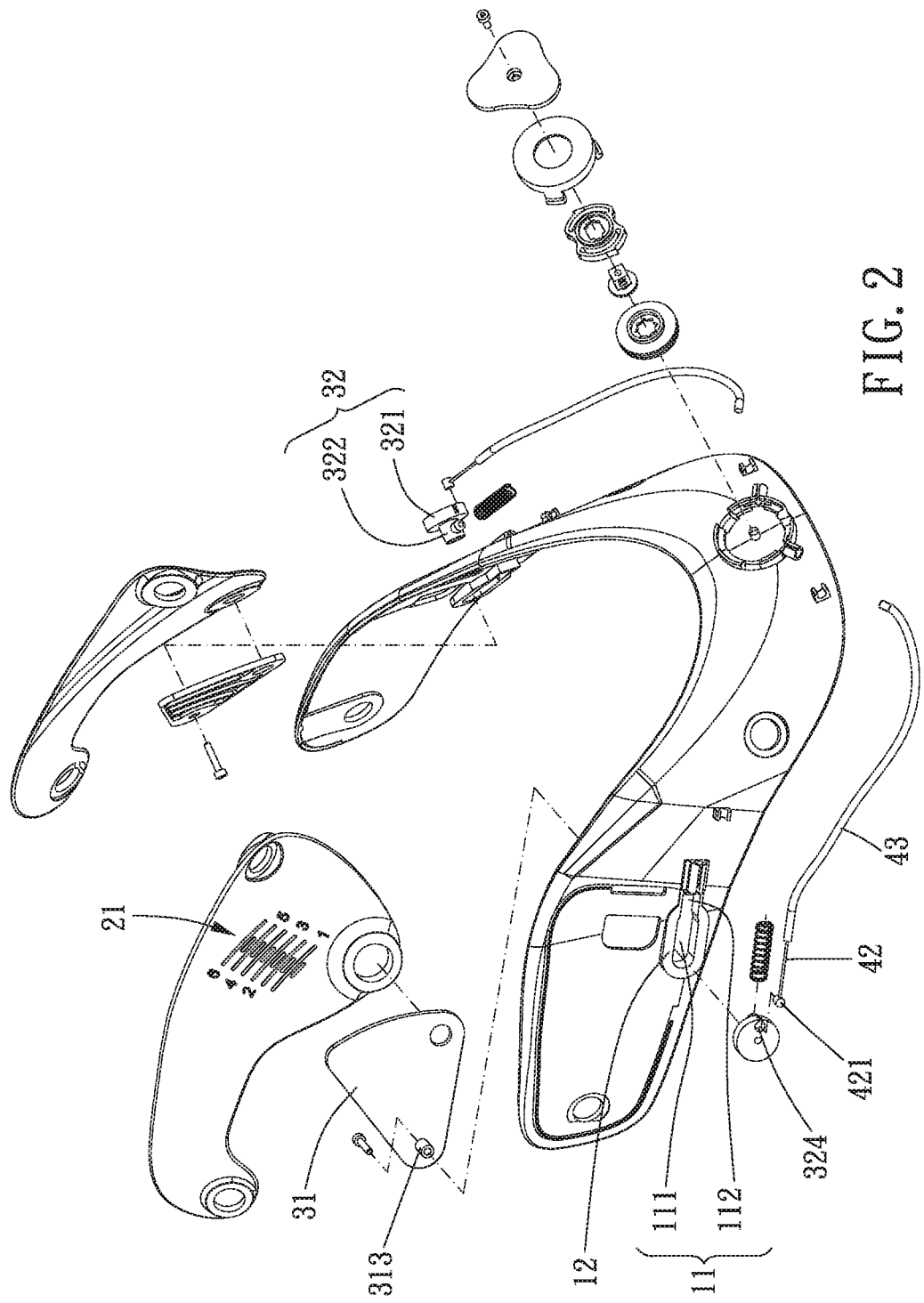
FIG. 2 is a breakdown drawing of a preferable embodiment of the present invention.
Figure 3:
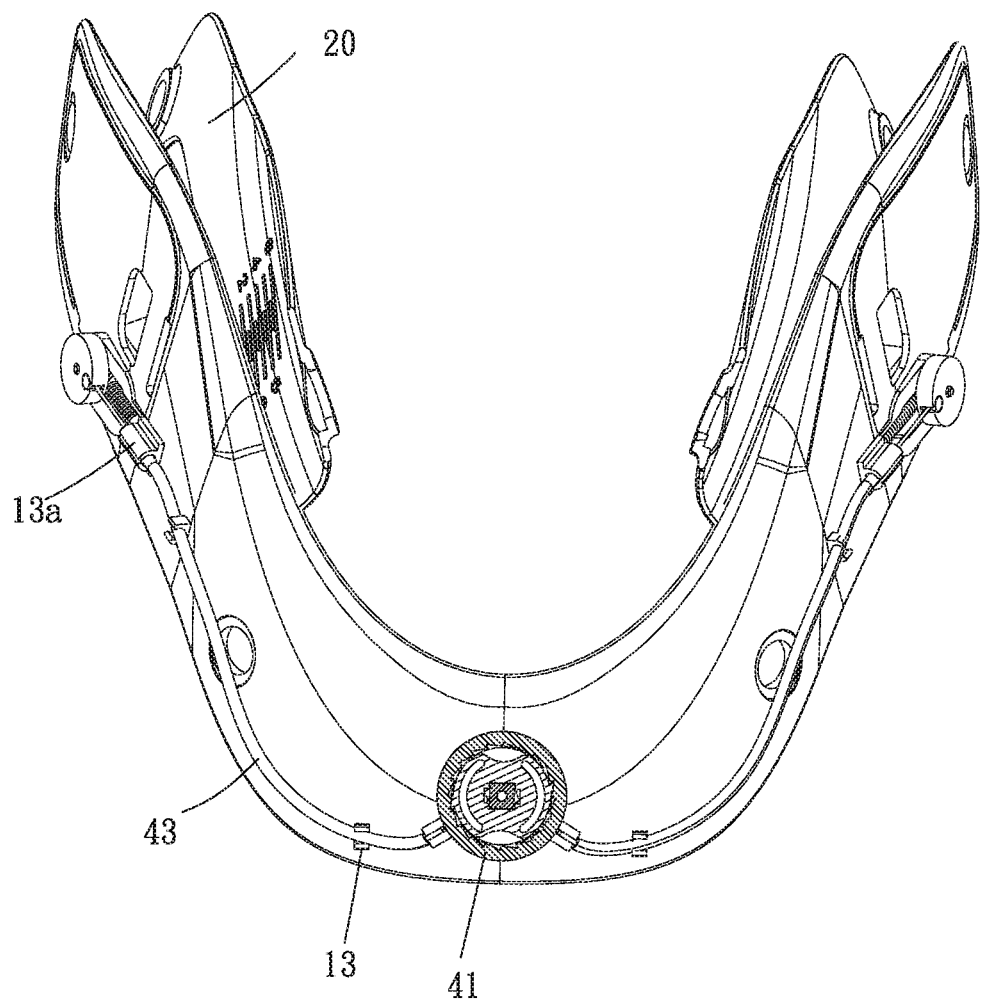
FIG. 3 is a front view of a preferable embodiment of the present invention.
Figure 4:
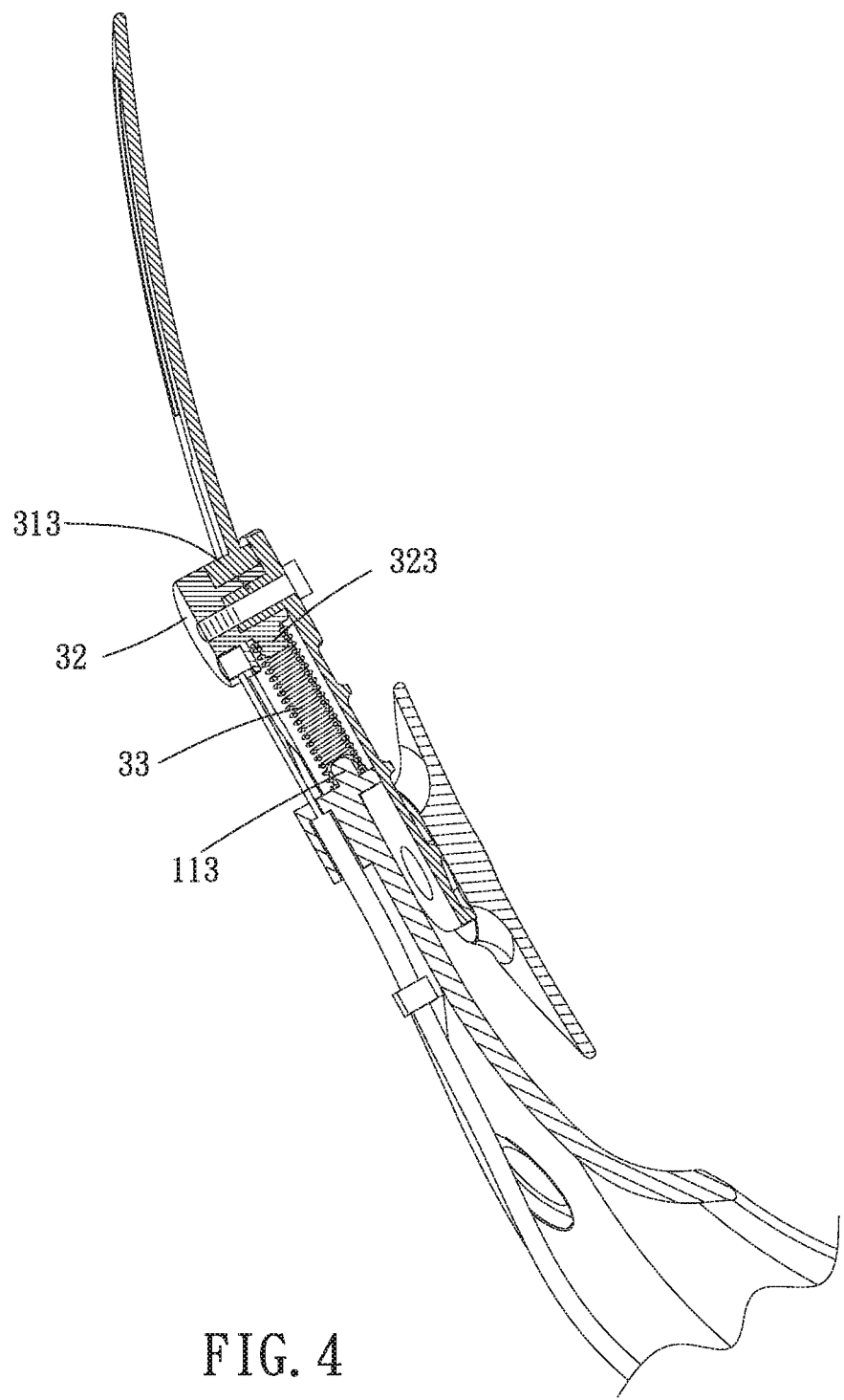
FIG. 4 is a partial cross-sectional view of a preferable embodiment of the present invention.
Figure 5:
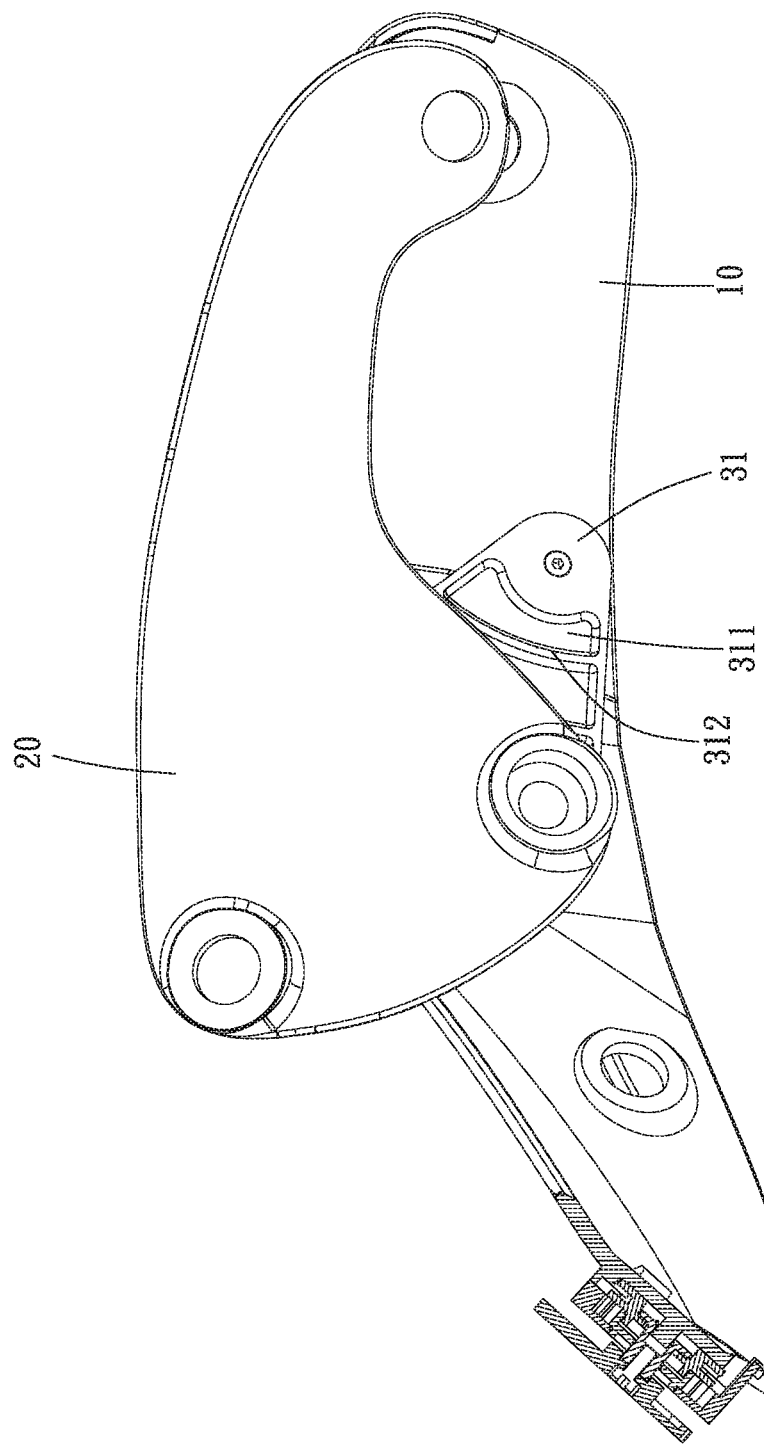
FIG. 5 is a partial side view of a preferable embodiment of the present invention.

Please refer to FIGS. 1 to 7 for a preferable embodiment of the present invention. A neck collar 1 of the present invention includes a neck sleeve 10, a chin support 20 and an adjustment mechanism 30.

The chin support 20 is swingably connected to the neck sleeve 10. The adjustment mechanism 30 includes at least one linking member 31 and at least one driving member 32 with which the at least one linking member 31 is co-movably connected. Each of the at least one linking member 31 is movably connected to the neck sleeve 10 and movably abutted against the chin support 20. The at least one driving member 32 is externally operable and adjustable to drive the at least one linking member 31 to move relative to the neck sleeve 10 and to move relative to the chin support 20, simultaneously, between a first position and a second position. When the at least one linking member 31 is moved from the first position toward the second position, the at least one linking member 31 drives the chin support 20 to swing upwardly relative to the neck sleeve 10. Therefore, the neck collar 1 has a simple structure and is smoothly adjustable.

The at least one linking member 31 is disposed between the neck sleeve 10 and the chin support 20 and swingable between the first position and the second position relative to the chin support 20, which has a simple structure and is easy to be adjusted. However, the at least one linking member may be abutted against the chin support by a guiding mechanism (such as a wedge structure, inclined surface or the like) so as to drive the chin support to swing. The chin support 20 preferably further has an indicating portion 21 disposed on a side facing toward the neck sleeve 10, and the indicating portion 21 may be a scale mark which is convenient for indication and adjustment. Each of the at least one linking member 31 is a sheet which has a plurality of recessions 311 disposed on a side facing toward the chin support 2 and a plurality of ribs 312 each extending between adjacent two of the plurality of recessions 311. The plurality of recessions 311 reduce frictions between the sheet and the chin support 20 for easy swinging, and the plurality of ribs 312 increase structural strength of the sheet.

The neck sleeve 10 has at least one guiding groove 11 disposed therethrough, and the at least one driving member 32 is slidably disposed within the at least one guiding groove 11 and rotatably connected with the at least one linking member 31. In this embodiment, each of the at least one linking member 31 has an assembling portion 313 protruding toward the at least one driving member 32, and the at least one driving member 32 is sleeved with the assembling portion 313 and rotatably connected with the at least one linking member 31 so that the at least one linking member 31 is stably rotatable relative to the at least one driving member 32. The neck sleeve 10 includes at least one thickened wall 12 disposed around the at least one guiding groove 11, and the thickened wall 12 may be integrally and protrudingly formed as a part of the neck sleeve 10 or be additionally attached to an outer periphery wall of the at least one guiding groove 11 so as to increase structural strength and improve abutment and operation with the at least one driving member 32.

The adjustment mechanism 30 further includes at least one elastic member 33 disposed between the at least one driving member 32 and an inner circumferential wall of the at least one guiding groove 11. The at least one elastic member 33 is abutted against the at least one driving member 32 to drive the at least one linking member 31 to move toward the first position. Specifically, each of the at least one driving member 32 includes a head portion 321 and a body portion 322 connected to the head portion 321, and each of the at least one guiding groove 11 includes a broadened segment 111 and a narrowed segment 112 which are communicated with each other. The body portion 322 is slidably disposed within the broadened segment 111, and the at least one elastic member 33 is disposed within the narrowed segment 112. A diametric dimension of the body portion 322 is smaller than a width of the broadened segment 111 and larger than a width of the narrowed segment 112 so as to restrict a range of movement of the at least one driving member 32.

Preferably, two engaging portions 113, 323 extending toward each other are respectively disposed on the at least one driving member 32 and the inner circumferential wall of the at least one guiding groove 11, and the at least one elastic member 33 is elastically abutted against and between the two engaging portions 113, 323. In this embodiment, each of the two engaging portions 113, 323 is a projection, and the body portion 322 has one of said projections radially extending toward the narrowed segment 112, and an inner circumferential wall of the narrowed segment 112 has the other of said projections extending toward the broadened segment 111 so that the at least one elastic member 33 is easy to assemble and position. In other embodiments, each of the two engaging portions may be a concave.

The neck collar 1 further includes a reel device 40 disposed on the neck sleeve 10. Each of two opposite sides of the neck sleeve 10 has one of said linking member 31 and one of said driving member 32. The reel device 40 includes a reel member 41 and a line member 42 wound around the reel member 41, and each of two ends of the line member 42 has a first engaging portion 421 which is detachably engageable with a second engaging portion 324 disposed on one of two said driving members 32. In this embodiment, each of two said first engaging portions 421 is an engaging convex and each of two said second engaging portions 324 is an engaging concave within which the engaging convex is received for stable engagement and easy maintenance and replacement. The reel device 40 further includes two guiding sheathes 43 sleeved on the line member 42, and the neck sleeve 10 has a plurality of positioning members 13, 13a which are disposed between the reel member 41 and the at least one guiding groove 11. Each of the two guiding sheathes 43 extends between the reel member 41 and the at least one guiding groove 11 and is releasably engaged within the plurality of positioning members 13, 13a. Therefore, the two guiding sheathes 43 effectively position and protect the line member 42, and the line member 42 has preferable force transmission effect. Preferably, the narrowed segment 112 of each of the at least one guiding groove 11 is adjacent to one of the plurality of positioning members 13a, which ensures that the line member 42 pulls the driving member 32 along an extending direction of the guiding groove 11.

Figure 6:
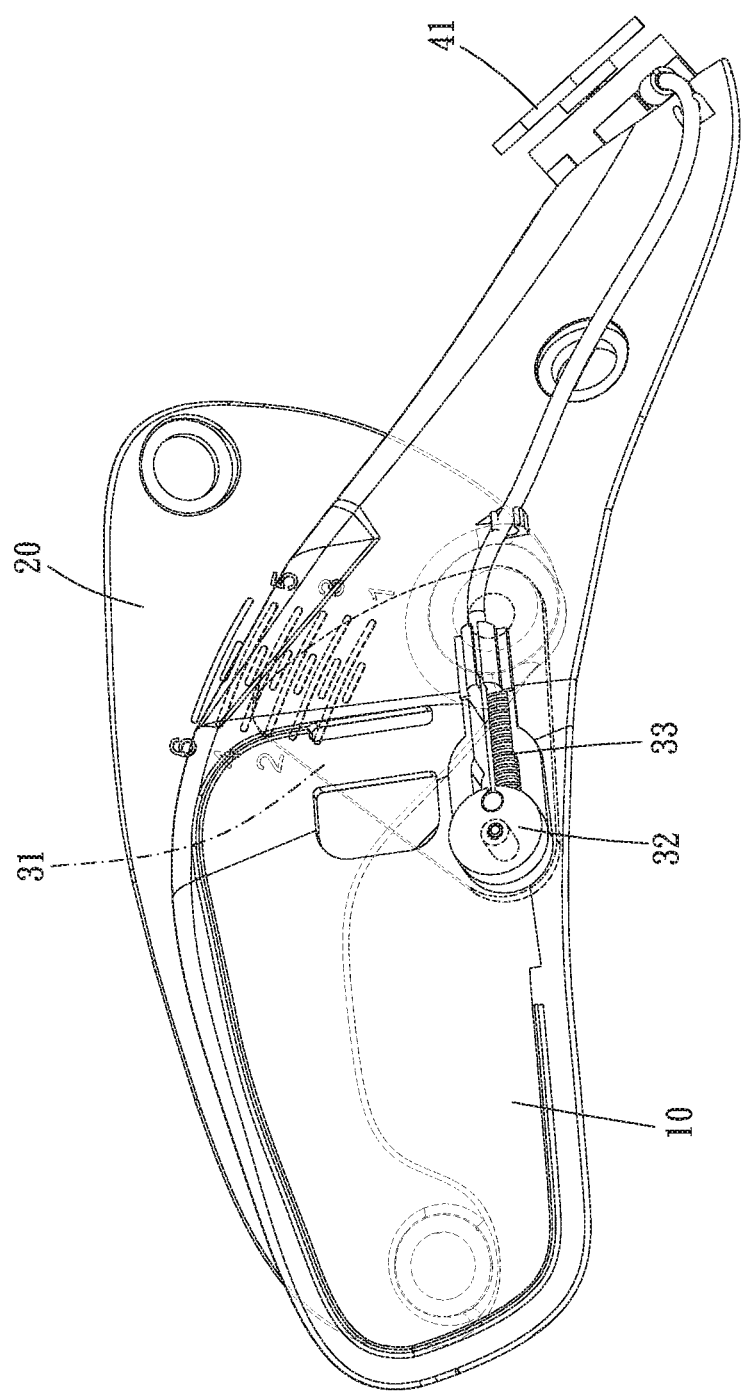
FIGS. 6 and 7 are schematic diagrams of a preferable embodiment of the present invention in operation.
Figure 7:
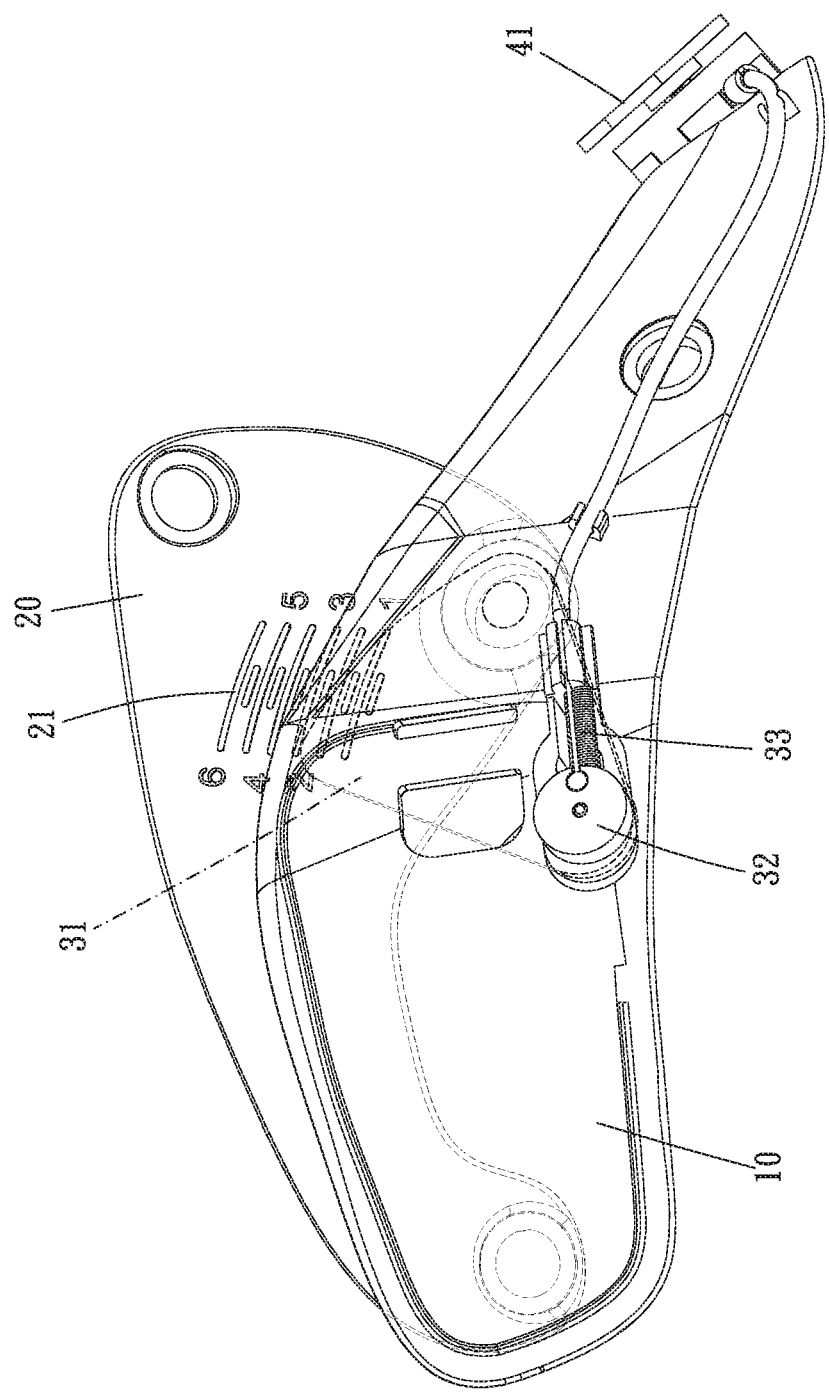

Refer to FIGS. 6 and 7, in operation, the reel member 41 simultaneously drives the two said driving members 32 to move from the first position toward the second position, and each of the two said driving members 32 presses one of said elastic member 33 and drives one of two said linking members 31 to move relative to the neck sleeve 10 and swing relative to the chin support 20 so as to drive the chin support 20 to swing upwardly, which is easy to operate.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A neck collar, including:
   a neck sleeve;
   a chin support, swingably connected to the neck sleeve;
   an adjustment mechanism, including at least one linking member and at least one driving member with which the at least one linking member is co-movably connected, each of the at least one linking member being movably connected to the neck sleeve and movably abutted against the chin support, the at least one driving member being externally operable and adjustable to drive the at least one linking member to move relative to the neck sleeve and to move relative to the chin support, simultaneously, between a first position and a second position;
   wherein when the at least one linking member is moved from the first position toward the second position, the at least one linking member drives the chin support to swing upwardly relative to the neck sleeve; the neck sleeve has at least one guiding groove disposed therethrough, and the at least one driving member is slidably disposed within the at least one guiding groove and rotatably connected with the at least one linking member; wherein the adjustment mechanism further includes at least one elastic member disposed between the at least one driving member and an inner circumferential wall of the at least one guiding groove, and the at least one elastic member is abutted against the at least one driving member to drive the at least one linking member to move toward the first position; wherein two engaging portions extending toward each other are respectively disposed on the at least one driving member and the inner circumferential wall of the at least one guiding groove, and the at least one elastic member is elastically abutted against and between the two engaging portions and wherein the neck sleeve includes at least one thickened wall disposed around the at least one guiding groove; each of the at least one driving member incudes a head portion and a body portion connected to the head portion, each of the at least one guiding groove includes a broadened segment and a narrowed segment which are communicated with each other, the body portion is slidably disposed within the broadened segment, and a diametric dimension of the body portion is smaller than a width of the broadened segment and larger than a width of the narrowed segment; each of the two engaging portions is a projection, the body portion has one of two said projections radially extending toward the narrowed segment, and an inner circumferential wall of the narrowed segment has the other of the two said projections extending toward the broadened segment; each of the at least one linking member has an assembling portion protruding toward the at least one driving member, the at least one driving member is sleeved to the assembling portion and rotatably connected with the at least one linking member; the neck collar further includes a reel device disposed on the neck sleeve, two opposite sides of the neck sleeve respectively have one of said linking member and one of said driving member, the reel device includes a reel member and a line member wound around the reel member, two ends of the line member respectively have a first engaging portion which is detachably engageable with a second engaging portion disposed on one of two said driving members; each of two said first engaging portions is an engaging convex, and each of two said second engaging portions is an engaging concave within which the engaging convex is received; the chin support further has an indicating portion disposed on a side facing toward the neck sleeve; each of two said linking members is a sheet which has a plurality of recessions disposed on a side facing toward the chin support and a plurality of ribs each extending between adjacent two of the plurality of recessions; the reel device further includes two guiding sheathes sleeved on the line member, the neck sleeve has a plurality of positioning members which are disposed between the reel member and the at least one guiding groove, each of the two guiding sheathes extends between the reel member and the at least one guiding groove and is releasably engaged within the plurality of positioning members; the narrowed segment of each of the at least one guiding groove is adjacent to one of the plurality of positioning members.

2. The neck collar of claim 1, wherein the neck sleeve includes at least one thickened wall disposed around the at least one guiding groove.

3. The neck collar of claim 1, wherein each of the at least one driving member includes a head portion and a body portion connected to the head portion, each of the at least one guiding groove includes a broadened segment and a narrowed segment which are communicated with each other, the body portion is slidably disposed within the broadened segment, and a diametric dimension of the body portion is smaller than a width of the broadened segment and larger than a width of the narrowed segment.

4. The neck collar of claim 1, wherein each of the at least one linking member has an assembling portion protruding toward the at least one driving member, and the at least one driving member is sleeved with the assembling portion and rotatably connected with the at least one linking member.

5. The neck collar of claim 1, further including a reel device disposed on the neck sleeve, wherein each of two opposite sides of the neck sleeve has one of said linking member and one of said driving member, the reel device includes a reel member and a line member wound around the reel member, and each of two ends of the line member has a first engaging portion which is detachably engageable with a second engaging portion disposed on one of two said driving members.

6. The neck collar of claim 1, wherein the at least one linking member is disposed between the neck sleeve and the chin support and swingable between the first position and the second position relative to the chin support.

* * * * *